United States Patent [19]

Kranz et al.

[11] 4,291,047
[45] Sep. 22, 1981

[54] COMBATING FUNGI WITH α-AZOLYL-β-HYDROXY-KETONES

[75] Inventors: Eckart Kranz; Wolfgang Krämer; Karl H. Büchel, all of Wuppertal; Wilhelm Brandes, Leichlingen; Paul-Ernst Frohberger, Leverkusen, all of Fed. Rep. of Germany

[73] Assignee: Bayer Aktiengesellschaft, Leverkusen, Fed. Rep. of Germany

[21] Appl. No.: 54,061

[22] Filed: Jul. 2, 1979

[30] Foreign Application Priority Data

Jul. 21, 1978 [DE] Fed. Rep. of Germany ....... 2832233

[51] Int. Cl.³ .................... A01N 43/64; A01N 43/50; C07D 249/08; C07D 233/60
[52] U.S. Cl. .............................. 424/273 R; 424/269; 424/245; 548/262; 548/341; 548/101
[58] Field of Search .............................. 548/341, 262; 424/273 R, 269

[56] References Cited

U.S. PATENT DOCUMENTS

| | | | |
|---|---|---|---|
| 3,812,142 | 5/1974 | Meiser et al. | 548/341 |
| 3,843,667 | 10/1974 | Cupery | 548/341 X |
| 3,952,002 | 4/1976 | Kramer et al. | 424/269 X |
| 4,113,465 | 9/1978 | Shephard et al. | 548/262 X |
| 4,217,129 | 8/1980 | Shephard et al. | 548/341 |

FOREIGN PATENT DOCUMENTS

| | | |
|---|---|---|
| 2201063 | 6/1977 | Fed. Rep. of Germany . |
| 2713022 | 9/1977 | Fed. Rep. of Germany . |
| 2734426 | 2/1978 | Fed. Rep. of Germany . |
| 2737489 | 2/1978 | Fed. Rep. of Germany . |
| 2819879 | 11/1978 | Fed. Rep. of Germany ...... 548/262 |

*Primary Examiner*—Richard A. Schwartz
*Attorney, Agent, or Firm*—Sprung, Felfe, Horn, Lynch & Kramer

[57] ABSTRACT

α-Azolyl-β-hydroxy-ketones of the formula

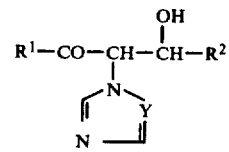

in which $R^1$ represents optionally substituted alkyl or optionally substituted phenyl, $R^2$ represents the grouping —$CX^1X^2R^3$ or alkoxycarbonyl, $R^3$ represents halogen, halogenoalkyl or optionally substituted phenyl, $X^1$ and $X^2$, which may be identical or different, each represents hydrogen or halogen, and Y represents a nitrogen atom or the CH group, or physiologically acceptable acid-addition salts or metal-salt complexes thereof which possess fungicidal properties.

10 Claims, No Drawings

COMBATING FUNGI WITH α-AZOLYL-β-HYDROXY-KETONES

The present invention relates to and has for its objects the provision of particular new α-azolyl-β-hydroxyketones which possess fungicidal properties, active compositions in the form of mixtures or such compounds with solid and liquid dispersible carrier vehicles, and methods for producing such compounds and for using such compounds in a new way especially for combating pests, e.g. fungi, with other and further objects becoming apparent from a study of the within specification and accompanying examples.

It has already been disclosed that substituted phenoxy-triazolyl-keto derivatives and -hydroxy derivatives in general have very good fungicidal properties (see DE-AS (German Published Specification) No. 2,201,063 and DE-OS (German Published Specification) No. 2,324,010). However, in some specific fields of application, their action is not always completely satisfactory, especially when low amounts and concentrations are used.

The present invention now provides as new compounds the α-azolyl-β-hydroxy-ketones of the general formula

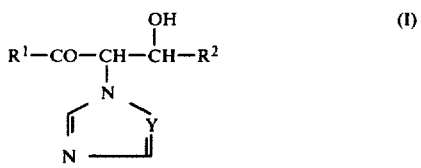

(I)

in which $R^1$ represents optionally substituted alkyl or optionally substituted phenyl, $R^2$ represents the grouping —$CX^1X^2R^3$ or alkoxycarbonyl, $R^3$ represents halogen, halogenoalkyl or optionally substituted phenyl, $X^1$ and $X^2$, which may be identical or different, each represent hydrogen or halogen and Y represents a nitrogen atom or the CH group, and the physiologically acceptable acid-addition salts and metal-salt complexes thereof. They display powerful fungicidal properties, in particular systemic fungicidal properties.

Preferably, in formula (I), $R^1$ represents optionally substituted straight-chain or branched alkyl with 1 to 4 carbon atoms, preferred substituents being: halogen (especially fluorine, chlorine and bromine), alkylcarbonyloxy with 1 to 4 carbon atoms in the alkyl part; optionally substituted phenylcarbonyloxy [preferred substituents being halogen (especially fluorine, chlorine and bromine), alkyl with 1 to 2 carbon atoms, halogenoalkyl with 1 to 2 carbon atoms and 1 to 5 halogen atoms (especially fluorine and/or chlorine), cyano and nitro]; alkyl- or dialkylcarbamoyloxy with 1 to 4 carbon atoms in the or each alkyl part, alkylsulphonyloxy with 1 to 4 carbon atoms, optionally substituted phenylsulphonyloxy [preferred substituents on the phenyl part being halogen (especially fluorine, chlorine and bromine), alkyl with 1 to 2 carbon atoms, halogenoalkyl with 1 to 2 carbon atoms and 1 to 5 halogen atoms (especially fluorine and/or chlorine), cyano and nitro], dialkylaminosulphonyloxy with 1 to 4 carbon atoms in each alkyl part; alkoxy with 1 to 4 carbon atoms, optionally substituted phenoxy [preferred substituents being halogen (especially fluorine, chlorine and bromine), alkyl with 1 to 2 carbon atoms, halogenoalkyl with 1 to 2 carbon atoms and 1 to 5 halogen atoms (especially fluorine and/or chlorine), cyano and nitro]; or phenyl which is optionally monosubstituted or polysubstituted by identical or different substituents [preferred substituents being halogen (especially fluorine, chlorine and bromine), cyano, nitro, straight-chain or branched alkyl with up to 4 carbon atoms, cycloalkyl with 5 to 7 carbon atoms (especially cyclohexyl), halogenoalkyl with up to 2 carbon atoms and up to 5 halogen atoms (especially fluorine atoms and chlorine atoms), phenyl, phenoxy and benzyl, the three last-mentioned radicals themselves being optionally substituted by halogen (especially fluorine or chlorine), cyano or nitro];

$R^2$ represents the grouping —$CX^1X^2R^3$ or alkoxycarbonyl with 1 to 4 carbon atoms in the alkoxy part;

$R^3$ represents halogen (especially fluorine, chlorine or bromine), halogenoalkyl with 1 to 4 carbon atoms and 1 to 3 halogen atoms (especially fluorine, chlorine or bromine) or optionally substituted phenyl [preferred substituents being halogen (especially fluorine, chlorine or bromine), alkyl with 1 to 2 carbon atoms, halogenoalkyl with 1 to 2 carbon atoms and 1 to 5 halogen atoms (especially fluorine or chlorine), cyano and nitro];

$X^1$ and $X^2$ are identical or different and each represent hydrogen, chlorine, fluorine or bromine; and Y represents a nitrogen atom or the CH group.

The compounds of the formula (I) have two asymmetric carbon atoms; they can therefore exist in the erythro-form and in the threo-form. In both cases, they exist predominantly as racemates.

Surprisingly, the α-azolyl-β-hydroxy-ketones according to the invention exhibit a considerably higher fungicidal activity, especially when used systemically against varieties of scab and powdery mildew, than the substituted phenoxy-triazolyl-keto derivatives and -hydroxy derivatives, which are known from the state of the art and are closely related compounds chemically and from the point of view of their action. The substances according to the invention thus represent an enrichment of the art.

Particularly preferred compounds are those of the formula (I) in which $R^1$ represents tert.-butyl, sec.-butyl, isopropyl, chloro-tert.-butyl, bromo-tert.-butyl, fluoro-tert.-butyl, 1,3-dichloro-2-methyl-prop-2-yl, 2-methylcarbamoyloxy-prop-2-yl, 2-diethylcarbamoyloxy-prop-2-yl, methylsulphonyloxy-tert.-butyl, phenylsulphonyloxy-tert.-butyl, 4-chlorophenylsulphonyloxy-tert.-butyl, acetoxy-tert.-butyl, ethylcarbonyloxy-tert.-butyl, phenylcarbonyloxy-tert.-butyl, 4-chlorophenylcarbonyloxy-tert.-butyl, diethylaminosulphonyloxy-tert.-butyl, methoxy-tert.-butyl, ethoxy-tert.-butyl, isopropoxy tert.-butyl, phenoxy-tert.-butyl, 4-chlorophenoxy-tert.-butyl, phenyl, chlorophenyl, dichlorophenyl, chloro-methylphenyl, bromophenyl, nitrophenyl, biphenylyl, nitrobiphenylyl, chlorobiphenylyl, phenoxyphenyl, chlorophenoxyphenyl, benzylphenyl or chlorobenzylphenyl; $R^2$ represents trichloromethyl, dichlorofluoromethyl, dichloromethyl, chloromethyl, 1,1,2-tribromoethyl, 1,1-dibromoethyl, 1,1-dichloro-eth-1-yl, 1,1,2-trichloro-prop-1-yl, phenyldichloromethyl, 4-chlorophenyldichloromethyl, methoxycarbonyl or ethoxycarbonyl; and Y represents a nitrogen atom or the CH group.

Specific compounds of the general formula (I) which may be mentioned, in addition to the compounds indicated in the preparative examples given later in this specification, are the following:

TABLE 1

$$R^1-CO-CH(OH)-CH(R^2)-N(\text{-N=CH-Y=CH-})\quad (I)$$

(1,2,4-triazol-1-yl or imidazol-1-yl ring attached via N)

| $R^1$ | $R^2$ | Y |
|---|---|---|
| C6H5— | —CO—O—C2H5 | N |
| 2,4-Cl2-C6H3— | —CO—O—C2H5 | N |
| 4-Cl-C6H4— | —CO—O—C2H5 | N |
| 4-Cl-C6H4— | —CCl2—CHCl—CH3 | N |
| 4-C6H5-C6H4— (biphenyl) | —CCl2—CHCl—CH3 | N |
| 4-C6H5-C6H4— | —CO—O—C2H5 | N |
| 4-C6H5-C6H4— | —CCl3 | N |
| 4-Cl-C6H4-C6H4— | —CCl3 | N |
| 4-Cl-C6H4-C6H4— | —CO—O—C2H5 | N |
| 4-Cl-C6H4-C6H4— | —CCl2—CHCl—CH3 | N |
| 2,4-Cl2-C6H3— | —CCl3 | N |
| 2,4-Cl2-C6H3— | —CO—O—C2H5 | N |
| 2,4-Cl2-C6H3— | —CCl2—CHCl—CH3 | N |
| 4-C6H5O-C6H4— | —CCl3 | N |
| 4-C6H5O-C6H4— | —CO—O—C2H5 | N |
| 4-C6H5O-C6H4— | —CCl2—CHCl—CH3 | N |
| 4-Br-C6H4— | —CCl3 | N |
| 4-Br-C6H4— | —CO—O—C2H5 | N |
| 4-Br-C6H4— | —CCl2—CHCl—CH3 | N |
| 4-NO2-C6H4-C6H4— | —CCl3 | N |

TABLE 1-continued

| $R^1$ | $R^2$ | Y |
|---|---|---|
| 4-NO2-C6H4-C6H4— | —CO—O—C2H5 | N |
| 4-NO2-C6H4-C6H4— | —CCl2—CHCl—CH3 | N |
| ClCH2—C(CH3)2— | —CCl2—CHCl—CH3 | N |
| ClCH2—C(CH3)2— | —CO—O—C2H5 | N |
| FCH2—C(CH3)2— | —CCl3 | N |
| FCH2—C(CH3)2— | —CO—O—C2H5 | N |
| FCH2—C(CH3)2— | —CCl2—CHCl—CH3 | N |
| CH3NH—CO—O—C(CH3)2— | —CCl3 | N |
| CH3NH—CO—O—C(CH3)2— | —CO—O—C2H5 | N |
| CH3NH—CO—O—C(CH3)2— | —CCl2—CHCl—CH3 | N |
| CH3—SO2—O—CH2—C(CH3)2— | —CCl3 | N |
| CH3—SO2—O—CH2—C(CH3)2— | —CO—O—C2H5 | N |
| CH3—SO2—O—CH2—C(CH3)2— | —CCl2—CHCl—CH3 | N |
| CH3—CO—O—CH2—C(CH3)2— | —CCl3 | N |
| CH3—CO—O—CH2—C(CH3)2— | —CO—O—C2H5 | N |
| CH3—CO—O—CH2—C(CH3)2— | —CCl2—CHCl—CH3 | N |
| Br—CH2—C(CH3)2— | —CCl2—CHCl—CH3 | N |
| Br—CH2—C(CH3)2— | —CO—O—C2H5 | N |
| 4-Cl-2-CH3-C6H3— | —CCl3 | N |
| 4-Cl-2-CH3-C6H3— | —CO—O—C2H5 | N |
| 4-Cl-2-CH3-C6H3— | —CCl2—CHCl—CH3 | N |
| CH3O—C(CH3)2— | —CCl3 | N |
| CH3O—C(CH3)2— | —CO—O—C2H5 | N |
| CH3O—C(CH3)2— | —CCl2—CHCl—CH3 | N |
| C2H5O—C(CH3)2— | —CCl3 | N |
| C2H5O—C(CH3)2— | —CO—O—C2H5 | N |
| C2H5O—C(CH3)2— | —CCl2—CHCl—CH3 | N |
| C6H5—O—C(CH3)2— | —CCl3 | N |
| C6H5—O—C(CH3)2— | —CO—O—C2H5 | N |
| C6H5—O—C(CH3)2— | —CCl2—CHCl—CH3 | N |
| C(CH3)3 | —CO—O—C2H5 | CH |
| 2,4-Cl2-C6H3— | —CO—O—C2H5 | CH |
| 4-Cl-C6H4— | —CO—O—C2H5 | CH |

TABLE 1-continued $$R^1-CO-CH-\underset{\underset{N}{|}}{\overset{OH}{\underset{|}{CH}}}-R^2 \quad (I)$$

(with N-Y-CH ring attached)

| $R^1$ | $R^2$ | Y |
|---|---|---|
| (biphenyl) | —CO—O—C₂H₅ | CH |
| (biphenyl) | —CCl₂—CHCl—CH₃ | CH |
| Cl—(biphenyl) | —CCl₃ | CH |
| Cl—(biphenyl) | —CO—O—C₂H₅ | CH |
| Cl—(biphenyl) | —CCl₂—CHCl—CH₃ | CH |
| Cl,Cl-(phenyl) | —CCl₃ | CH |
| Cl,Cl-(phenyl) | —CO—O—C₂H₅ | CH |
| Cl,Cl-(phenyl) | —CCl₂—CHCl—CH₃ | CH |
| Cl-(phenyl)-O-(phenyl) | —CCl₃ | CH |
| Cl-(phenyl)-O-(phenyl) | —CCl₂—CHCl—CH₃ | CH |
| Cl-(phenyl)-O-(phenyl) | —CO—O—C₂H₅ | CH |
| (phenyl)-O-(phenyl) | —CCl₃ | CH |
| (phenyl)-O-(phenyl) | —CO—O—C₂H₅ | CH |
| (phenyl)-O-(phenyl) | —CCl₂—CHCl—CH₃ | CH |
| Br-(phenyl) | —CCl₃ | CH |
| Br-(phenyl) | —CO—O—C₂H₅ | CH |
| Br-(phenyl) | —CCl₂—CHCl—CH₃ | CH |
| NO₂-(biphenyl) | —CCl₃ | CH |
| NO₂-(biphenyl) | —CO—O—C₂H₅ | CH |
| NO₂-(biphenyl) | —CCl₂—CHCl—CH₃ | CH |
| Cl,CH₃-(phenyl) | —CCl₃ | CH |
| Cl,CH₃-(phenyl) | —CO—O—C₂H₅ | CH |
| Cl,CH₃-(phenyl) | —CCl₂—CHCl—CH₃ | CH |
| Cl—CH₂—C(CH₃)₃— | —CCl₃ | CH |
| Cl—CH₂—C(CH₃)₂— | —CO—O—C₂H₅ | CH |
| Cl—CH₂—C(CH₃)₂— | —CCl₂—CHCl—CH₃ | CH |
| CH₃—CO—O—CH₂—C(CH₃)₂— | —CCl₃ | CH |
| CH₃—CO—O—CH₂—C(CH₃)₂— | —CO—O—C₂H₅ | CH |
| CH₃—CO—O—CH₂—C(CH₃)₂— | —CCl₂—CHCl—CH₃ | CH |
| CH₃NH—CO—O—C(CH₃)₂— | —CCl₃ | CH |
| CH₃NH—CO—O—C(CH₃)₂— | —CO—O—C₂H₅ | CH |
| CH₃NH—CO—O—C(CH₃)₂— | —CCl₂—CHCl—CH₃ | CH |
| CH₃—SO₂—O—CH₂—C(CH₃)₂— | —CCl₃ | CH |
| CH₃—SO₂—O—CH₂—C(CH₃)₂— | —CO—O—C₂H₅ | CH |
| CH₃—SO₂—O—CH₂—C(CH₃)₂— | —CCl₂—CHCl—CH₃ | CH |
| Br—CH₂—C(CH₃)₂— | —CO—O—C₂H₅ | CH |
| Br—CH₂—C(CH₃)₂— | —CCl₂—CHCl—CH₃ | CH |
| FCH₂—C(CH₃)₂— | —CCl₃ | CH |
| FCH₂—C(CH₃)₂— | —CO—O—C₂H₅ | CH |
| FCH₂—C(CH₃)₂— | —CCl₂—CHCl—CH₃ | CH |
| CH₃O—C(CH₃)₂— | —CCl₃ | CH |
| CH₃O—C(CH₃)₂— | —CO—O—C₂H₅ | CH |
| CH₃O—C(CH₃)₂— | —CCl₂—CHCl—CH₃ | CH |
| C₂H₅O—C(CH₃)₂— | —CCl₃ | CH |
| C₂H₅O—C(CH₃)₂— | —CO—O—C₂H₅ | CH |
| C₂H₅O—C(CH₃)₂— | —CCl₂—CHCl—CH₃ | CH |
| (phenyl)-O-C(CH₃)₂— | —CCl₃ | CH |
| (phenyl)-O-C(CH₃)₂— | —CO—O—C₂H₅ | CH |
| (phenyl)-O-C(CH₃)₂— | —CCl₂—CHCl—CH₃ | CH |

The invention also provides a process for the preparation of an α-azolyl-β-hydroxy-ketone of the formula (I), in which an α-azolyl-ketone of the general formula

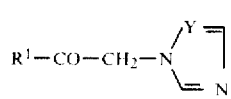

(II)

in which $R^1$ and Y have the meanings stated above, is reacted with an aldehyde of the general formula

in which $R^2$ has the meanings stated above, in the present of a solvent and in the presence of a catalyst.

In some cases, it is also possible to employ the aldehydes of the formula (III) in the form of their hydrates or hemi-acetals.

Furthermore, the α-azolyl-β-hydroxy-ketones of the formula (I) obtainable according to the invention can be converted into salts by reaction with acids, or the corresponding metal salt complexes can be obtained by reaction with metal salts.

If, for example 3,3-dimethyl-1-(1,2,4-triazol-1-yl)butan-2-one and chloral are used as starting materials, the course of the reaction can be represented by the equation which follows:

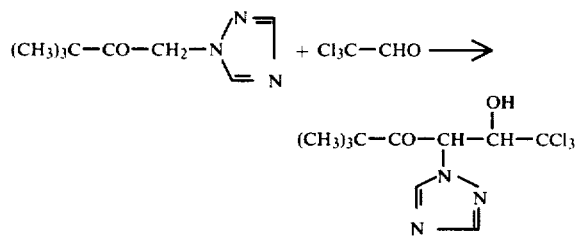

The formula (II) provides a general definition of the α-azolyl-ketones to be used as starting substances for the process according to the invention. In this formula, $R^1$ and Y preferably represent those radicals which have already been mentioned as preferred in the case of the compounds of the formula (I).

Some of the α-azolyl-ketones of the formula (II) are known (see DE-OS (German Published Specification) No. 2,063,857 and DE-OS (German Published Specification) No. 2,431,407. Those which have not yet been described in the literature can be obtained by the processes described therein, for example by (a) reacting halogenoketones of the general formula

in which
$R^1$ has the meaning stated above and
Hal represents chlorine and bromine, with 1,2,4-triazole or imidazole in the presence of an inert organic solvent, for example acetone, and in the presence of an acid-binding agent, for example sodium carbonate, preferably at the boil (see also the preparative examples), (b) reacting hydroxyketones of the general formula

in which $R^1$ has the meaning stated above, with thionyl-bisazoles of the general formula

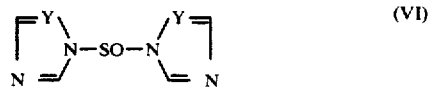

in which Y has the meaning stated above, in the presence of a polar organic solvent, for example acetonitrile, preferably at the boil.

Examples which may be mentioned of the starting materials of the formula (II) are (azolyl representing 1,2,4-triazol-1-yl or imidazol-1-yl): 1-azolyl-3,3-dimethyl-butan-2-one, 1-azolyl-4-chloro-3,3-dimethyl-butan-2-one, 1-azolyl-4-bromo-3,3-dimethyl-butan-2-one, 1-azolyl-4-fluoro-3,3-dimethyl-butan-2-one, 1-azolyl-4-acetoxy-3,3-dimethyl-butan-2-one, 1-azolyl-4-ethylcarbonyloxy-3,3-dimethyl-butan-2-one, 1-azolyl-4-methylsulphonyloxy-3,3-dimethyl-butan-2-one, 1-azolyl-4-phenylsulphonyloxy-3,3-dimethyl-butan-2-one, 1-azolyl-4-diethylaminosulphonyloxy-3,3-dimethyl-butan-2-one, 1-azolyl-4-methoxy-3,3-dimethylbutan-2-one, 1-azolyl-4-ethoxy-3,3-dimethyl-butan-2-one, 1-azolyl-4-phenoxy-3,3-dimethyl-butan-2-one, 1-azolyl-3-diethylcarbamoyloxy-3-methyl-butan-2-one, 1-azolyl-3-methylcarbamoyloxy-3-methyl-butan-2-one, ω-azolylacetophenone, ω-azolyl-4-chloroacetophenone, ω-azolyl-4-bromoacetophenone, ω-azolyl-2,4-dichloroacetophenone, ω-azolyl-4-chloro-2-methylacetophenone, ω-azolyl-3,4-dichloroacetophenone, ω-azolyl-4-phenylacetophenone, ω-azolyl-4-phenoxyacetophenone, ω-azolyl-4-benzylacetophenone, ω-azolyl-4-(4'-chlorophenyl)-acetophenone, ω-azolyl-4-(4'-chlorophenoxy)-acetophenone, ω-azolyl-4-(4'-chlorobenzyl)-acetophenone, ω-azolyl-4-(4'-nitrophenyl)-acetophenone and ω-azolyl-4-(4'-nitrophenoxy)-acetophenone.

The formula (III) provides a general definition of the aldehydes also to be used as starting substances for the reaction according to the invention. In this formula, $R^2$ preferably represents those radicals which already have been mentioned as preferred in the case of the compounds of the formula (I).

The aldehydes of the formula (III) are generally known compounds of organic chemistry. Examples which may be mentioned are: chloral, dichlorofluoroacetaldehyde, 2,2,3-trichlorobutyraldehyde, 2,2-dichloropropionaldehyde, glyoxylic acid methyl ester, glyoxylic acid ethyl ester, dichloroacetaldehyde, chloroacetaldehyde, 2,2-dibromopropionaldehyde and 2,2,3-tribromopropionaldehyde.

Preferred solvents for the reaction according to the invention are inert organic solvents, especially alcohols, such as methanol and ethanol, and mixtures thereof with water; ethers, such as tetrahydrofuran and dioxane; nitriles, such as acetonitrile and propionitrile; halogenated aliphatic and aromatic hydrocarbons, such as methylene chloride, carbon tetrachloride, chloroform, chlorobenzene and dichlorobenzene; and glacial acetic acid.

The reaction according to the invention is carried out in the presence of a catalyst. It is possible to employ all the acidic and, in particular, basic catalysts which can customarily be used. Preferred catalysts include Lewis acids, for example iron-(III) chloride, iron-(III) bromide, boron trifluoride, boron trichloride, tin tetrachloride or titanium tetrachloride; alkali metal hydroxides and alkaline earth metal hydroxides, such as potassium hydroxide, sodium hydroxide, calcium hydroxide or barium hydroxide; alkali metal salts, such as potassium carbonate, sodium carbonate, potassium cyanide, secondary sodium phosphate, sodium acetate or sodium sulphite; and alcoholates, such as sodium methylate or potassium methylate.

The reaction temperatures can be varied within a substantial range in carrying out the process according to the invention. In general, the process is carried out at from 0° to 100° C., preferably at room temperature or at the boiling point of the particular solvent.

Equimolar amounts of the reactants are preferably used in carrying out the process according to the invention, catalytic to equimolar amounts of the catalyst being employed. Isolation of the compounds of the formula (I) is effected in the customary manner (see also the preparative examples).

All the physiologically acceptable acids can be used for the preparation of acid-addition salts of the compounds of the formula (I). Preferred acids include the hydrogen halide acids (for example hydrobromic acid and especially hydrochloric acid), phosphoric acid, nitric acid, sulphuric acid, monofunctional and bifunctional carboxylic acids and hydroxycarboxylic acids (for example acetic acid, maleic acid, succinic acid, fumaric acid, tartaric acid, citric acid, salicylic acid, sorbic acid and lactic acid) and sulphonic acids (for example p-toluenesulphonic acid and 1,5-naphthalenedisulphonic acid).

The salts of the compounds of the formula (I) can be obtained in a simple manner by customary salt-formation methods, for example by dissolving a compound of the formula (I) in a suitable inert solvent and adding the acid, for example hydrochloric acid, and they can be isolated in a known manner, for example by filtration, and optionally purified by washing with an inert organic solvent.

Salts of metals of main groups II to IV and of subgroups I and II and IV to VIII of the Periodic Table can preferably be used for the preparation of metal-salt complexes of the compounds of the formula (I), examples of metals which may be mentioned being copper, zinc, manganese, magnesium, tin, iron and nickel. Possible anions of the salts are those which are derived from physiological acids, preferably the hydrogen halide acids (for example hydrochloric acid and hydrobromic acid), phosphoric acid, nitric acid and sulphuric acid.

The metal-salt complexes of the compounds of the formula (I) can be obtained in a simple manner by customary processes, for example by dissolving the metal salt in alcohol, for example ethanol, and adding the solution to the compound of the formula (I). The metal-salt complexes can be isolated in a known manner, for example by filtration, and optionally purified by recrystallization.

The active compounds according to the invention exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

The good toleration by plants of the active compounds, at the concentrations required for combating plant diseases, permits treatment of above-ground parts of plants, of vegetative propagation stock and seed, and of the soil.

As plant protection agents, the active compounds according to the invention can be used with particuarly good success for combating those fungi which cause powdery mildew diseases, for instance for combating Erysiphe species, for example the powdery mildew of cucumber causative organism (*Erysiphe cichoracearum*) or the powdery mildew of barley or powdery mildew of cereal causative organism (*Erysiphe graminis*); and for combating those fungi which cause scab diseases, for instance, for combating Venturia species, for example the apple scab causative organism (*Fusicladium dendriticum*). It should be particularly emphasised that the active compounds according to the invention not only develop a protective action, but, in particular, also have a systemic action. Thus, it is possible to protect plants against fungal attack when the active compound is fed to the above-ground parts of the plant via the soil and the root or via the seed.

The active compounds can be converted into the customary formulations, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in the formulations or in the various use forms as a mixture with other known active compounds, such as fungicides, bactericides, insecticides, acaricides, nematicides, herbicides, bird repellents, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They may be used in the customary manner, for example by watering, immersion, spraying, atomizing, misting, vaporising, injecting, forming a slurry, brushing on, dusting, scattering, dry dressing, moist dressing, wet dressing, slurry dressing or encrusting.

Especially in the treatment of parts of plants, the active compound concentrations in the use forms can be varied within a substantial range. They are, in general, from 1 to 0.0001% by weight, preferably from 0.5 to 0.001%.

In the treatment of seed, amounts of active compound of 0.001 to 50 g, preferably 0.01 to 10 g, are generally employed per kilogram of seed.

For the treatment of soil, active compound concentrations of 0.00001 to 0.1% by weight, preferably 0.0001 to 0.02%, are required at the place of action.

The present invention also provides a fungicidal composition containing as active ingredient a compound of the present invention in admixture with a solid or liquefied gaseous diluent or carrier or in admixture with a liquid diluent or carrier containing a surface-active agent.

The present invention also provides a method of combating fungi which comprises applying to the fungi, or to a habitat thereof, a compound of the present invention alone or in the form of a composition containing as active ingredient a compound of the present invention in admixture with a diluent or carrier.

The present invention further provides crops protected from damage by fungi by being grown in areas in which immediately prior to and/or during the time of the growing a compound of the present invention was applied alone or in admixture with a diluent or carrier.

It will be seen that the usual methods of providing harvested crop may be improved by the present invention.

The invention will be further described in the following illustrative examples:

EXAMPLE 1

(a)

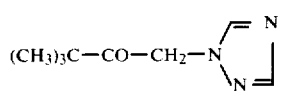

138 g (2 mol) of 1,2,4-triazole were added in portions to 276.4 g (2 mol) of ground potassium carbonate and 269.2 g (2 mol) of α-chloropinacolin in 500 ml of acetone at room temperature, during which the internal temperature rose to the boiling point. The mixture was stirred under reflux for 5 hours and then cooled to room temperature. The reaction mixture was filtered and the filtrate was concentrated by distilling off the solvent in vacuo. After adding benzine, the oily residue crystallized. 240.8 g (72% of theory) of 3,3-dimethyl-1-(1,2,4-triazol-1-yl)-butan-2-one of melting point 62°–64° C. were obtained.

(b)

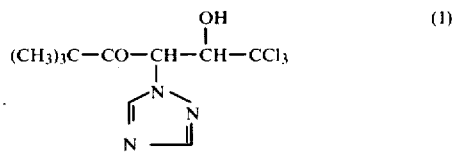

33.4 g (0.2 mol) of 3,3-dimethyl-1-(1,2,4-triazol-1-yl)-butan-2-one were dissolved in 150 ml of methylene chloride and the solution was cooled to −5° C. 19 g (0.1 mol) of titanium tetrachloride, and then 29.5 g (0.2 mol) of chloral, were slowly added dropwise to this solution. The internal temperature was kept constant at −5° C. during the metering. Thereafter, the mixture was warmed slowly to the reflux and stirred for 3 hours. The reaction solution was poured onto ice and the white curdy precipitate which formed was filtered off. After boiling up in 250 ml of methanol and then drying, 19.9 g (32% of theory) of 1,1,1-trichloro-2-hydroxy-3-(1,2,4-triazol-1-yl)-5,5-dimethyl-hexan-4-one of melting point 220°–222° C. were obtained.

EXAMPLE 2

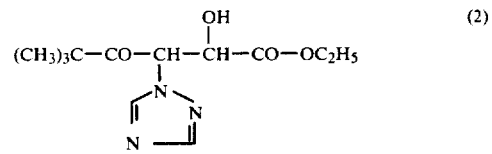

16.7 g (0.1 mol) of 3,3-dimethyl-1-(1,2,4-triazol-1-yl)-butan-2-one were dissolved in 400 ml of water. A solution of 29.6 g (0.2 mol) of glyoxylic acid ethyl hemiacetal in 100 ml of methanol was added to this solution. 28 ml of 10% strength sodium hydroxide solution were added dropwise at room temperature. The mixture was subsequently stirred for 48 hours, the reaction solution was then extracted three times with 200 ml of ethyl acetate each time and the combined organic phases were dried over sodium sulphate. After distilling off the solvent in vacuo, a yellow oil which crystallized slowly was obtained. After stirring the product with 50 ml of diethyl ether, 6.1 g (23% of theory) of 5,5-dimethyl-2-hydroxy-4-oxo-3-(1,2,4-triazol-1-yl)-hexanecarboxylic acid ethyl ester of melting point 102°–109° C. were obtained.

EXAMPLE 3

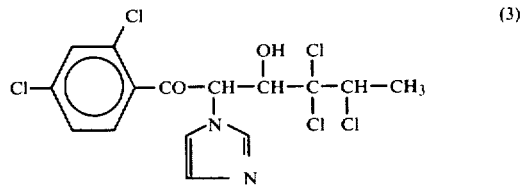

A mixture of 31.6 g (0.124 mol) of ω-imidazol-1-yl-2,4-dichloroacetophenone, 2.06 g (0.025 mol) of anhydrous sodium acetate, 18 g (0.3 mol) of glacial acetic acid and 19.3 g (0.1 mol) of 2,2,3-trichlorobutyraldehyde was stirred at room temperature for 15 hours.

Thereafter, the glacial acetic acid was distilled off in vacuo and the residue was stirred with 200 ml of diethyl ether and 200 ml of water. The crystalline reaction product which separated out between the two phases was filtered off and dried. 32.3 g (75% of theory) of 2,4-dichlorophenyl (2,3,3-trichloro-4-hydroxy-5-imidazol-1-yl)-pent-5-yl ketone of melting point 138°–140° C. were obtained.

EXAMPLE 4

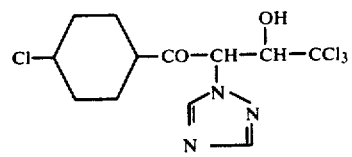

14.76 g (0.1 mol) of chloral are added dropwise to a mixture of 22.2 g (0.1 mol) of ω-(1,2,4-triazol-1-yl)-4-chloroacetophenone, 5.1 g (0.063 mol) of anhydrous sodium acetate and 45.4 g (0.68 mol) of glacial acetic acid at room temperature, whilst stirring. The mixture is subsequently stirred at 100° C. for 20 hours. Thereafter, the precipitate is filtered off, washed with 100 ml portions of diethyl ether, extracted by stirring with 150 ml of methanol and dried. 22.1 g (60% of theory) of 4-chlorophenyl 1,1,1-trichloro-2-hydroxy-3-(1,2,4-triazol-1-yl)propyl ketone of melting point 173°–174° C. were obtained.

The compounds in the table which follows, of the general formula

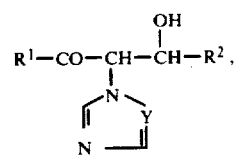

were obtained in a corresponding manner:

TABLE 2

| Compound No. | $R^1$ | $R^2$ | Y | Melting point (°C.) |
|---|---|---|---|---|
| 5 | $(CH_3)_3C-$ | $-CO-OC_2H_5$ | N | 146–49 (pure isomer) |
| 6 | $(CH_3)_3C-$ | $-CCl_2-CHCl-CH_3$ | N | 198–204 |
| 7 | $ClCH_2-C(CH_3)_2-$ | $-CCl_3$ | N | 171–72 |
| 8 | $BrCH_2-C(CH_3)_2-$ | $-CCl_3$ | N | 169–71 |
| 9 | phenyl | $-CCl_3$ | N | 195–97 |
| 10 | phenyl | $-CCl_2-CHCl-CH_3$ | N | 170–72 |
| 11 | 2,4-dichlorophenyl | $-CCl_3$ | N | 167–69 |
| 12 | 2,4-dichlorophenyl | $-CCl_2-CHCl-CH_3$ | N | 158–62 |
| 13 | 4-chlorophenoxyphenyl | $-CCl_3$ | N | 184–86 |
| 14 | $(CH_3)_3C-$ | $-CCl_3$ | CH | 135–38 |
| 15 | $(CH_3)_3C-$ | $-CCl_2-CHCl-CH_3$ | CH | 165–66 |
| 16 | $BrCH_2-C(CH_3)_2-$ | $-CCl_3$ | CH | 132–34 |
| 17 | phenyl | $-CCl_3$ | CH | 151–52 |
| 18 | phenyl | $-CCl_2-CHCl-CH_3$ | CH | 140–41 |
| 19 | phenyl | $-CO-OC_2H_5$ | CH | 160–62 |
| 20 | 2,4-dichlorophenyl | $-CCl_3$ | CH | 141–42 |
| 21 | 4-chlorophenyl | $-CCl_3$ | CH | 145–47 |
| 22 | 4-chlorophenyl | $-CCl_2-CHCl-CH_3$ | CH | 129–31 |
| 23 | biphenyl | $-CCl_3$ | CH | 145–49 |
| 24 | 4-chlorophenoxyphenyl | $-CCl_3$ | CH | 147–49 |
| 25 | $BrCH_2-C(CH_3)_2-$ | $-CCl_2-CHCl-CH_3$ | CH | 138–39 |
| 26 | $(CH_3)_3C-$ | $-CCl_3$ | N | 155–56 |

TABLE 2-continued

| Compound No. | R¹ | R² | Y | Melting point (°C.) |
|---|---|---|---|---|
| 27 | (CH₃)₃C— | —CCl₃ | CH | 108–12 (× CuCl₂) |
| 28 | Cl—⟨C₆H₄⟩—⟨C₆H₄⟩— | —CCl₃ | CH | 233–36 (× ½CuCl₂) |
| 29 | Cl—⟨C₆H₄⟩— | —CCl₃ | CH | 118–20 |
| 30 | ⟨C₆H₅⟩— | —CCl₂—CHCl—CH₃ | CH | 116–20 (× ½CuCl₂) |
| 31 | ⟨C₆H₅⟩— | —CO—OC₂H₅ | CH | 102–08 (× ½CuCl₂) |
| 32 | 3,4-Cl₂—⟨C₆H₃⟩— | —CCl₂—CHCl—CH₃ | CH | 96–98 (× ½CuCl₂) |
| 33 | Br—⟨C₆H₄⟩— | —CCl₃ | CH | 151–53 |
| 34 | ClCH₂—C(CH₃)₂— | —CCl₃ | N | 145–50 (× CuCl₂) |
| 35 | 3,4-Cl₂—⟨C₆H₃⟩— | —CCl₂—CHCl—CH₃ | N | 161–63 (× CuCl₂) |
| 36 | Cl—⟨C₆H₄⟩— | —CCl₃ | N | 89–93 (× CuCl₂) |
| 37 | (CH₃)₃C— | —CCl₂—CHCl—CH₃ | N | 100–05 (× CuCl₂) |
| 38 | BrCH₂—C(CH₃)₂— | —CCl₃ | N | 143–45 (× CuCl₂) |
| 39 | 3,4-Cl₂—⟨C₆H₃⟩— | —CCl₃ | N | 96–104 (× CuCl₂) |
| 40 | FCH₂—C(CH₃)₂— | —CCl₃ | N | 121–24 (× CuCl₂) |
| 41 | FCH₂—C(CH₃)₂— | —CHCl₂ | N | 121–23 (× CuCl₂) |
| 42 | (CH₃)₃C— | —CCl₂—CH₂Cl | N | |
| 43 | ClCH₂—C(CH₃)₂— | —CCl₃ | CH | 141–43 |
| 44 | ClCH₂—C(CH₃)₂— | —CCl₂—CHCl—CH₃ | CH | 146–47 |
| 45 | Br—⟨C₆H₄⟩— | —CCl₂—CHCl—CH₃ | CH | 145–47 |
| 46 | ⟨C₆H₅⟩—O—⟨C₆H₄⟩— | —CCl₃ | CH | 161–64 |
| 47 | 3,4-Cl₂—⟨C₆H₃⟩— | —CCl₃ | CH | 155–56 |
| 48 | 3,4-Cl₂—⟨C₆H₃⟩— | —CCl₂—CHCl—CH₃ | CH | 136–37 |
| 49 | (CH₃)₃C— | —CCl₂—CHCl—CH₃ | N | 204–10 |
| 50 | (CH₃)₃C— | —CF₃ | N | 179–80 |
| 51 | (CH₃)₃C— | —CCl(CH₃)₂ | N | 165–66 |
| 52 | (CH₃)₃C— | —CHCl₂ | N | 188–90 |
| 53 | (CH₃)₃C— | —CO—OCH₃ | N | 150–55 |
| 54 | (CH₃)₃C— | —CO—OC₄H₉ | N | 110–14 (pure isomer) |
| 55 | (CH₃)₃C— | —CO—OC₄H₉ | N | 107–08 |
| 56 | (CH₃)₃C— | —CHCl₂ | N | 164–65 (pure isomer) |
| 57 | ClCH₂—C(CH₃)₂— | —CHCl₂ | N | 172–74 |
| 58 | ClCH₂—C(CH₃)₂ | —CCl₂—CHCl—CH₃ | N | 169–73 |
| 59 | FCH₂—C(CH₃)₂— | —CCl₃ | N | 195–96 |
| 60 | FCH₂—C(CH₃)₂— | —CHCl₂ | N | 173–74 |
| 61 | ⟨C₆H₅⟩—O—⟨C₆H₄⟩— | —CCl₃ | N | 198–203 |
| 62 | 3-Cl,4-CH₃—⟨C₆H₃⟩— | —CCl₃ | N | 160–63 |
| 63 | Cl—⟨C₆H₄⟩— | —CCl₂—CH₂Cl | N | |

TABLE 2-continued

| Compound No. | R$^1$ | R$^2$ | Y | Melting point (°C.) |
|---|---|---|---|---|
| 64 | F—⟨O⟩— | —CCl$_3$ | CH | 141-44 |
| 65 | CH$_3$—SO$_2$—O—CH$_2$—C(CH$_3$)$_2$— | —CCl$_2$—CHClCH$_3$ | N | 140-48 |
| 66 | CH$_3$—⟨O⟩—SO$_2$—O—CH$_2$—C(CH$_3$)$_2$— | —CCl$_3$ | N | |
| 67 | CH$_3$—SO$_2$—O—CH$_2$—C(CH$_3$)$_2$— | —CCl$_2$—CH$_2$Cl | N | 155-60 |
| 68 | CH$_3$—SO$_2$—O—CH$_2$—C(CH$_3$)$_2$— | —CCl$_3$ | N | 151-55 |
| 69 | CH$_3$—CO—O—CH$_2$—C(CH$_3$)$_2$— | —CCl$_3$ | N | 177-85 |
| 70 | FCH$_2$—C(CH$_3$)$_2$— | —CO—OCH$_3$ | N | 128-30 |
| 71 | ClCH$_2$—C(CH$_3$)$_2$— | —CO—OCH$_3$ | N | |
| 72 | FCH$_2$—C(CH$_3$)$_2$— | —CCl(CH$_3$)$_2$ | N | |
| 73 | ClCH$_2$—C(CH$_3$)$_2$— | —CCl$_2$—CH$_2$Cl | N | oil |
| 74 | F—⟨O⟩— | —CCl$_3$ | N | 181-82 |
| 75 | (CH$_3$)$_3$C— | —CCl$_2$—CH$_2$Cl | N | 191-94 |
| 76 | FCH$_2$—C(CH$_3$)$_2$— | —CCl$_2$—CH$_2$Cl | N | 167-70 |
| 77 | F—⟨O⟩— | —CCl$_3$ | CH | 107-11 (× CuCl$_2$) |
| 78 | (CH$_3$)$_3$C— | —CCl$_2$—CH$_2$Cl | N | 98-105 (× CuCl$_2$) |
| 79 | (CH$_3$)$_3$C— | —CCl(CH$_3$)$_2$ | N | (× CuCl$_2$) |
| 80 | CH$_3$—SO$_2$—O—CH$_2$—C(CH$_3$)$_2$— | —CCl$_3$ | N | 85-96 (× CuCl$_2$) |
| 81 | FCH$_2$—C(CH$_3$)$_2$— | —CCl$_2$—CHClCH$_3$ | N | 97-101 (× CuCl$_2$) |

The fungicidal activity of the compounds of this invention is illustrated by the following examples wherein the compounds according to the present invention are each identified by the number (given in brackets) from the preparative examples hereinabove:

EXAMPLE 5

Erysiphe test (cucumber)/systemic

Solvent: 4.7 parts by weight of acetone
Emulsifier: 0.3 part by weight of alkylaryl polyglycol ether
Water: 95 parts by weight The amount of active compound required to give the desired concentration of active compound in the watering liquid was mixed with the stated amount of solvent and the concentrate was diluted with the stated amount of water which contained the stated amount of emulsifier.

Cucumber plants grown in standard soil, in the 1-2 leaf stage, were watered three times within one week with 10 ml of the watering liquid, of the stated concentration of active compound, per 100 ml of soil.

The plants treated in this way were inoculated, after treatment, with conidia of the fungus *Erysiphe cichoracearum*. The plants were then set up in a greenhouse at 23-24 degrees C. and 70% relative atmospheric humidity. After 12 days, the infection of the cucumber plants was determined. The assessment data were converted to percent infection. 0% denoted no infection and 100% denoted that the plants were completely infected.

In this test, for example, the following compounds exhibited a very good action, which was superior to that of the compounds known from the prior art: (14) and (1).

EXAMPLE 6

Fusicladium test (apple)/systemic

Solvent: 4.7 parts by weight of acetone
Emulsifier: 0.3 part by weight of alkylaryl polyglycol ether
Water: 95 parts by weight The amount of active compound required for the desired concentration of the active compound in the spray liquid was mixed with the stated amount of solvent, and the concentrate was diluted with the stated amount of water which contained the stated amount of emulsifier.

Apple seedlings grown in standard soil, in the 3 to 4 leaf stage, were watered once within one week with 10 ml of the watering liquid, of the prescribed concentration of active compound, per 100 ml of soil.

The plants treated in this way were inoculated, after treatment, with an aqueous conidia suspension of *Fusicladium dendriticum* and incubated for 18 hours in a humidity chamber at 18° to 20° C. and 100% relative atmospheric humidity. The plants were then again brought into a greenhouse for 14 days.

15 days after inoculation, the infection of the seedlings was determined. The assessment data were converted to percent infection. 0% denoted no infection and 100% denoted that the plants were completely infected.

In this test, for example, the following compound (1) exhibited a very good action, which was superior to that of the compounds known from the prior art:

EXAMPLE 7

Shoot treatment test/powdery mildew of cereals (leaf-destructive mycosis)/protective To produce a suitable preparation of active compound, 0.25 part by weight of active compound was taken up in 25 parts by weight of dimethylformamide and 0.06 part by weight of alkylaryl polyglycol ether; 975 parts by weight of water were then added. The concentrate was diluted with water to the desired final concentration of the spray liquor.

To test for protective activity, single-leaved young barley plants of the Amsel variety were sprayed with the preparation of active compound until dew-moist. After drying, the barley plants were dusted with spores of *Erysiphe graminis var. hordei*.

After 6 days' dwell time of the plants at a temperature of 21-22 deg. C. and 80-90% atmospheric humidity the occurrence of mildew pustules on the plants was evaluated. The degree of infection was expressed as a percentage of the infection of the untreated control plants. 0% denoted no infection and 100% denoted the same degree of infection as in the case of the untreated control. The active compound was the more active, the lower was its degree of mildew infection.

In this test, for example, the following compounds exhibited a very good action, which was superior to that of the compounds known from the prior art: (14) and (1).

EXAMPLE 8

Powdery mildew of barley (*Erysiphe graminis var. hordei*) (fungal disease of cereal shoots)/systemic The active compound was used as a pulverulent seed treatment agent. This was prepared by extending the particular active compound with a mixture of equal parts by weight of talc and kieselguhr to give a finely pulverulent mixture of the desired concentration of active compound.

For the treatment of seed, barley seed was shaken with the extended active compound in a closed glass bottle. The seed was sown at the rate of 3×12 grains in flowerpots, 2 cm deep in a mixture of one part by volume of Fruhstorfer standard soil and one part by volume of quartz sand. The germination and emergence took place under favourable conditions in a greenhouse. 7 days after sowing, when the barley plants had developed their first leaf, they were dusted with fresh spores of *Erysiphe graminis var. hordei* and grown on at 21-22 deg. C. and 80-90% relative atmospheric humidity and 16 hours' exposure to light. The typical mildew pustules formed on the leaves over the course of 6 days.

The degree of infection was expressed as a percentage of the infection of the untreated control plants. Thus, 0% denoted no infection and 100% denoted the same degree of infection as in the case of the untreated control. The active compound was the more active, the lower was its degree of mildew infection.

In this test, for example, the following compound (7) exhibited a very good action, which was superior to that of the compounds known from the prior art.

It will be appreciated that the instant specification and examples are set forth by way of illustration and not limitation, and that various modifications and changes may be made without departing from the spirit and scope of the present invention.

What we claim is:

1. An α-azolyl-β-hydroxy-ketone of the formula

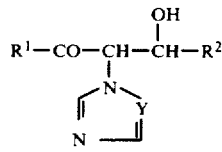

in which
R¹ is $C_{1-4}$-alkyl; $C_{1-4}$-alkyl substituted by halogen, $C_{1-4}$-alkyl carbonyl, phenylcarbonyloxy, halophenylcarbonyloxy, methylphenylcarbonyloxy, ethylphenylcarbonyloxy, cyanophenylcarbonyloxy, nitrophenylcarbonyloxy, halomethylphenylcarbonyloxy, haloethylphenylcarbonyloxy, $C_{1-4}$-alkylcarbamoyloxy, di-$C_{1-4}$-alkyl-carbamoyloxy, $C_{1-4}$-alkylsulphonyloxy, phenylsulphonyloxy, ethylphenylsulphonyloxy, halomethylphenylsulphonyloxy, haloethylphenylsulphonyloxy, cyanophenylsulphonyloxy, nitrophenylsulphonyloxy, di-$C_{1-4}$-alkylaminosulphonyloxy, $C_{1-4}$-alkoxy, phenoxy, halophenoxy, methylphenoxy, ethylphenoxy, halomethylphenoxy, haloethylphenoxy, cyanophenoxy or nitrophenoxy; phenyl; halophenyl; cyanophenyl; nitrophenyl; $C_{1-4}$-alkylphenyl; $C_{5-7}$cycloalkyl-phenyl; halomethylphenyl; haloethylphenyl; diphenyl; phenoxyphenyl; benzylphenyl; or halocyano-, and/or nitro-substituted diphenyl, phenoxyphenyl or benzylphenyl;

R² is $-CX^1X^2R^3$ or $C_{1-4}$-alkoxy-carbonyl;

R³ is halo; or halo-$C_{1-4}$-alkyl with up to 3 halogen atoms; and

X¹ and X², which may be identical or different, each represents hydrogen or halogen, and Y represents a nitrogen atom or the CH group, or a physiologically acceptable metal-salt complex thereof or addition salt with an acid selected from the group consisting of hydrochloric acid, hydrobromic acid, phosphoric acid, nitric acid, sulphuric acid, acetic acid, maleic acid, succinic acid, fumaric acid, tartaric acid, citric acid, salicylic acid, sorbic acid, lactic acid, p-toluenesulphonic acid and 1,5-naphthalenedisulphonic acid.

2. A compound according to claim 1, in which
X¹ and X² each independently is hydrogen, chlorine, fluorine, or bromine; or a pharmacologically acceptable salt thereof with an acid selected from the group consisting of hydrochloric acid, hydrobromic acid, phosphoric acid, nitric acid, sulphuric acid acetic acid, maleic acid, succinic acid, fumaric acid, tartaric acid, citric acid, salicylic acid, sorbic acid, lactic acid, p-toluenesulphonic acid and 1,5-naphthalenedisulphonic acid; or a metal salt complex thereof, the metal of the salt being selected from the main groups II to IV and sub-groups I, II and IV to VIII of the Periodic Table and the anion of the salt being derived from a hydrogen halide acid, sulphuric acid, nitric acid or phosphoric acid.

3. A compound acid addition salt or metal salt complex according to claim 1, in which R² is $-CX^1X^2R^3$.

4. A compound acid addition salt or metal salt complex according to claim 1, in which R² is trihalomethyl.

5. A compound or salt or complex thereof according to claim 1, in which said compound is 1,1,1-trichloro-2-hydroxy-3-(1,2,4-triazol-1-yl)-5,5-dimethyl-hexan-4-one of the formula

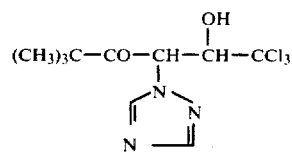

6. A compound or salt or complex thereof according to claim 1, in which said compound is 1,1,1-trichloro-2-hydroxy-3-(1,2,4-triazol-1-yl)-5-methyl-5-chloromethyl-hexan-4-one of the formula 7. A compound or salt or complex thereof according to claim 1, in which said compound is 1,1,1-trichloro-2-hydroxy-3-(imidazol-1-yl)-5,5-dimethyl-hexan-4-one of the formula

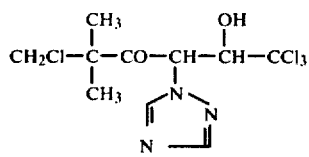

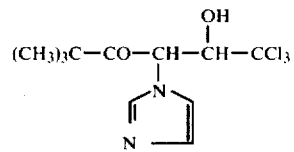

8. A fungicidal composition containing as active ingredient a fungicidally effective amount of a compound, salt or complex according to claim 1 in admixture with a diluent.

9. A method of combating fungi which comprises applying to the fungi, or to a habitat thereof, a fungicidally effective amount of a compound, salt or complex according to claim 1.

10. The method according to claim 9, in which said compound is 1,1,1-trichloro-2-hydroxy-3-(1,2,4-triazol-1-yl)-5,5-dimethyl-hexan-4-one,
1,1,1-trichloro-2-hydroxy-3-(1,2,4-triazol-1-yl)-5-methyl-5-chloromethyl-hexane-4-one, or
1,1,1-trichloro-2-hydroxy-3-(imidazol-1-yl)-5,5-dimethyl-hexan-4-one
or a salt or complex thereof.

* * * * *